United States Patent [19]

Tazi et al.

[11] Patent Number: 5,082,913

[45] Date of Patent: * Jan. 21, 1992

[54] TERPOLYMERS OF MALEIC ANHYDRIDE, ALKYL VINYL ETHERS AND ISOBUTYLENE AND CROSSLINKED PRODUCTS THEREOF

[75] Inventors: Mohammed Tazi, Wayne; Robert B. Login, Oakland, both of N.J.; Yoon T. Kwak, Brooklyn, N.Y.

[73] Assignee: ISP Investments Inc., Wilmington, Del.

[*] Notice: The portion of the term of this patent subsequent to Aug. 6, 2008 has been disclaimed.

[21] Appl. No.: 557,354

[22] Filed: Jul. 25, 1990

[51] Int. Cl.$^5$ .................. C08F 210/10; C08F 216/12; C08F 222/06
[52] U.S. Cl. ...................................... 526/272; 526/216
[58] Field of Search ............... 526/88, 271, 332, 348.7, 526/272

[56] References Cited

U.S. PATENT DOCUMENTS

| | | | |
|---|---|---|---|
| 4,370,454 | 1/1983 | Messmer et al. | 526/88 |
| 5,008,355 | 4/1991 | Tazi et al. | 526/271 |
| 5,037,924 | 8/1991 | Tazi et al. | 526/272 |

Primary Examiner—Mary C. Lee
Assistant Examiner—Fiona T. Powers
Attorney, Agent, or Firm—Walter Katz; Marilyn J. Maue; Joshua J. Ward

[57] ABSTRACT

Terpolymers of maleic anhydride, a $C_1$–$C_5$ alkyl vinyl ether and isobutylene, and crosslinked products thereof, are provided herein. The hydrophilic terpolymer compositions of the invention are particularly useful as denture adhesives while the hydrophobic terpolymer compositions find application as waterproofing materials.

4 Claims, No Drawings

TERPOLYMERS OF MALEIC ANHYDRIDE, ALKYL VINYL ETHERS AND ISOBUTYLENE AND CROSSLINKED PRODUCTS THEREOF

BACKGROUND OF THE INVENTION

1. Field of the Invention

This invention relates to terpolymers of maleic anhydride, a $C_1$–$C_5$ alkyl vinyl ether and a non-linear, unsaturated hydrocarbon, and, more particularly, to terpolymers of maleic anhydride, a $C_1$–$C_5$ alkyl vinyl ether and isobutylene, within defined compositional ranges, which are useful hydrophilic and hydrophobic terpolymers for application in denture and other adhesives, and as waterproofing agents, and to crosslinked products of such terpolymers, useful as thickeners and stabilizers.

2. Description of the Prior Art

Copolymers of maleic anhydride and alkyl vinyl ethers are well known in the art and are conventionally prepared by free radical precipitation polymerization of the monomer mixture in an aromatic hydrocarbon solvent such as benzene in the presence of a protective colloid. Another method involves copolymerization of maleic anhydride, an alkyl vinyl ether and/or a $C_3$–$C_{10}$ alkene in contact with a powder bed. In the latter method, disclosed in U.S. Pat. No. 4,370,454, a large excess of the alkyl vinyl ether and/or alkene, e.g. 3 to 25 moles, preferably 5 to 15 moles thereof, per mole of maleic anhydride monomer, is present during the polymerization, instead of the usual 1:1 mole ratio required of the copolymer. In the powder bed method, the heat generated during polymerization is removed by evaporating the excess alkyl vinyl ether and/or alkene which boils at a lower temperature than maleic anhydride. The examples in this patent were directed only to copolymers of maleic anhydride and alkyl vinyl ethers, or copolymers of maleic anhydride and alkene.

Accordingly, an object of the present invention is to provide terpolymers of maleic anhydride, a $C_1$–$C_5$ alkyl vinyl ether and isobutylene, within defined compositional ranges, predetermined for use in various applications, and by a conventional method of preparation.

Still another object herein is to provide hydrophilic terpolymers of maleic anhydride, a $C_1$–$C_5$ alkyl vinyl ether and isobutylene, and a process for making the same, which compositions are useful as adhesives, particularly denture adhesives.

Yet another object is to provide a hydrophobic terpolymer of maleic anhydride, a $C_1$–$C_5$ alkyl vinyl ether and isobutylene, which compositions are useful as waterproofing agents.

Another object of this invention is to provide a benzene-free process for making terpolymers of maleic anhydride, a $C_1$–$C_5$ alkyl vinyl ether and isobutylene of predetermined composition.

Still another object is to provide crosslinked products of the terpolymer of the invention, useful as thickeners and stabilizers.

These and other objects and features of the invention will be made apparent from the following description of the invention.

SUMMARY OF THE INVENTION

What is provided herein is a terpolymer of maleic anhydride, a $C_1$–$C_5$ alkyl vinyl ether and isobutylene in predetermined compositional ranges of each monomer for use in selected applications, and a process for making such terpolymers in a benzene-free solvent system.

The invention provides hydrophilic terpolymers which are particularly useful as denture adhesives, and hydrophobic terpolymers which find application as waterproofing agents.

Crosslinked terpolymers of maleic anhydride, a $C_1$–$C_5$ alkyl vinyl ether and isobutylene also are provided herein for these applications.

DETAILED DESCRIPTION OF THE INVENTION

In accordance with the present invention, there is provided terpolymers of maleic anhydride, a $C_1$–$C_5$ alkyl vinyl ether and isobutylene, within predetermined compositional ranges which are useful in commercial application, and a process for making such terpolymers. In this process, a suitable reactor is provided with appropriate inlet tubes, agitation means, and heater and temperature control means. The reactor is first purged with nitrogen to remove air from the system. Generally three separate purges are employed, at about 3 bars pressure and about 40° C. The reactor is precharged with maleic anhydride in a suitable solvent which may be an aromatic hydrocarbon such as benzene or toluene but is preferably a mixed solvent of a cycloaliphatic hydrocarbon such as cyclohexane and an ester of an aliphatic acid such as ethyl acetate. A solvent system which is a 50:50 mixture of cyclohexane and ethyl acetate is preferred.

The precharged reactor is purged with nitrogen at about 58° C. and then a polymerization initiator is introduced in three stages during the polymerization, generally at the beginning, after about 1½ hours and finally after about 3 hours, of a polymerization period of about 3 hours. Any suitable free-radical initiator may be used including but not limited to peroxides; however tertiary butyl or tertiary amylperoxy pivalate are preferred as initiators. The concentration of the initiator may vary widely, although suitably it comprises about 0.05 to 2% by weight of the maleic anhydride reactant.

Then, simultaneously with feeding of the initiator, the alkyl vinyl ether and isobutylene monomers are introduced separately or together into the precharged reactor at a controlled rate during the course of the polymerization.

Overall, the molar ratio of maleic anhydride to the combined alkyl vinyl ether and isobutylene monomers is set as about 1:1, although in practice about a 10% excess of the latter two monomers is used to ensure complete conversion of the maleic anhydride to the desired terpolymer. The molar amounts of alkyl vinyl ether present in the terpolymer is about 0.4–0.9, preferably 0.6–0.8, and the molar amounts of isobutylene present in the terpolymer is about 0.1–0.6, preferably about 0.2–0.5. Lower amounts of isobutylene in the terpolymer will provide hydrophilic terpolymers which are particularly useful for denture adhesives while higher amounts of isobutylene will provide hydrophobic terpolymers suitable for waterproofing use.

Of course, during the polymerization the reaction mixture is agitated effectively. At the conclusion of the polymerization, the reaction product is held at the polymerization temperature for about 1½ hours. Then excess alkyl vinyl ether is vented, the product is discharged and the terpolymer solid is recovered by filtration or precipitation after removal of solvent.

An alternative process for preparing the terpolymers of the invention involves precharging solvent only and feeding molten maleic anhydride from a separate feed tube. This procedure will reduce the overall time required for feeding the reactants.

EXAMPLE 1

Preparation of Terpolymer of Invention 65 g. (0.67 mole) of maleic anhydride in 194 g. of a 50:50 mixture of cyclohexane and ethyl acetate was precharged in a reactor equipped with suitable inlet tubes, agitation means, and heater and temperature control means, and the reactor was purged three times with nitrogen at 3 bars pressure and at 58° C. Then 0.217 g. of Lupersol 11 in 2 g. of a 50:50 mixture of cyclohexane and ethyl acetate was added. Simutaneously, a mixture of 28.9 g. (37.6 ml., 0.5 mole) of methyl vinyl ether and 9.3 g. (15.8 ml., 0.17 mole) of isobutylene was fed into the reactor over a period of 3 hours while agitating the reaction mixture at about 180 rpm. Two additional portions of initiator of 0.217 g. each were introduced after 1½ and 3 hours. The reactant monomers constitute a 20% solids mixture in this solvent system. The reactor then was held at 58° C. for 1½ hours, cooled, excess methyl vinyl ether was vented and the product was discharged from the reactor. The desired powder terpolymer was obtained by filtration; it had a molar ratio of maleic anhydride to methyl vinyl ether to isobutylene of 1:0.75:0.25, which was substantially the same ratio as the reactants used in the process.

EXAMPLES 2-12

The process of Example 1 was followed to provide the terpolymers of desired compositions using monomers of different feeding composition and in various solvent systems.

TABLE 1

Molar Composition of Reactant Monomers in Examples 2-12

| Ex. No. | Maleic Anhydride | Methyl Vinyl Ether | Isobutylene | Solvent |
|---|---|---|---|---|
| 2 | 1 | 0.85 | 0.25 | CH/EA |
| 3 | 1 | 0.80 | 0.25 | CH/EA |
| 4 | 1 | 0.55 | 0.55 | CH/EA |
| 5 | 1 | 0.60 | 0.60 | CH/EA |
| 6 | 1 | 0.50 | 0.50 | toluene |
| 7 | 1 | 0.82 | 0.28 | toluene |
| 8 | 1 | 0.75 | 0.25 | benzene |
| 9 | 1 | 0.83 | 0.28 | benzene |
| 10 | 1 | 0.88 | 0.28 | benzene |
| 11 | 1 | 0.50 | 0.50 | benzene |
| 12 | 1 | 0.25 | 0.75 | benzene |

The molar composition of the terpolymer obtained was substantially the same as that of charged reactant monomers in the process.

EXAMPLE 13

Preparation of Crosslinked Terpolymers of Invention 65.0 g. (0.663 mole) of maleic anhydride was precharged into a reactor with 5.33 g. (0.048 mole) of 1,7-octadiene and 535 g. of toluene. The reactor was purged with nitrogen and heated to 58° C. Then a mixture of 21.17 g. (27.67 ml., 0.365 mole) of methyl vinyl ether and 20.46 g. (34.81 ml., 0.365 mole) of isobutylene was admitted into the reactor slowly over a period of 4 hours. Simultaneously, three portions of 0.65 g. each of Lupersol 11 was admitted during the polymerization of 4 hours. Then the reaction product was held at 58° C. for 1 hour, cooled to room temperature, excess methyl vinyl ether was vented and the product was filtered. 100.5 g. of dry terpolymer powder was collected.

The crosslinked terpolymer obtained in this manner had a molar ratio of maleic anhydride to methyl vinyl ether to isobutylene of 1:0.50:0.50 and was crosslinked with 5.0% by weight of 1,7-octadiene based on the total weight of the terpolymer.

EXAMPLE 14

The terpolymer was crosslinked with other crosslinking agents selected from dienes, divinyl ethers and allyl carbohydrates with similar results.

EXAMPLE 15

The 1,7-octadiene crosslinker was introduced with the externally fed monomers. The reaction product slurry was thick but filterable, and it was dried at 65° C. in vacuum oven. 98.9 g. of a dry product comprising the crosslinked terpolymer was obtained.

While the invention has been described with particular reference to certain embodiments thereof, it will be understood that changes and modifications may be made which are within the skill of the art. Accordingly, it is intended to be bound only by the following claims, in which:

What is claimed is:

1. A terpolymer of maleic anhydride, a $C_1$–$C_5$ alkyl vinyl ether and isobutylene in the molar ratio of about 1:0.4–0.9:0.1–0.6.

2. A terpolymer of maleic anhydride, a $C_1$–$C_5$ alkyl vinyl ether and isobutylene in the molar ratio of about 1:0.5–0.8:0.2–0.5.

3. A terpolymer of maleic anhydride, methyl vinyl ether and isobutylene in the molar ratio of about 1:0.4–0.9:0.1–0.6.

4. A terpolymer according to claim 1 which is crosslinked with a crosslinking agent.

* * * * *